United States Patent
Wong et al.

[11] Patent Number: 5,413,572
[45] Date of Patent: May 9, 1995

[54] OSMOTIC DOSAGE SYSTEM FOR LIQUID DRUG DELIVERY

[75] Inventors: Patrick S. L. Wong, Palo Alto; Felix Theeuwes, Los Altos; Brian L. Barclay, Sunnyvale; Michael H. Dealey, San Francisco, all of Calif.

[73] Assignee: Alza Corporation, Palo Alto, Calif.

[21] Appl. No.: 203,135

[22] Filed: Feb. 18, 1994

Related U.S. Application Data

[63] Continuation of Ser. No. 502,705, Apr. 2, 1990, Pat. No. 5,324,280.

[51] Int. Cl.⁶ .................................... A61K 9/22
[52] U.S. Cl. .................... 604/892.1; 424/453; 424/463; 424/468; 424/472
[58] Field of Search ............ 604/890.1–892.1; 424/422, 427, 438, 453, 462, 463, 468, 471, 472, 474, 482

[56] References Cited

U.S. PATENT DOCUMENTS

| | | | |
|---|---|---|---|
| 3,760,805 | 9/1973 | Higuchi | 604/892.1 |
| 3,995,631 | 12/1976 | Higuchi et al. | 604/892.1 |
| 4,138,013 | 2/1979 | Okajima | 424/453 |
| 4,180,073 | 12/1979 | Michaels | 604/892.1 |
| 4,203,440 | 5/1980 | Theeuwes | 604/892.1 |
| 4,203,441 | 5/1980 | Theeuwes | 604/892.1 |
| 4,203,442 | 5/1980 | Michaels | 604/892.1 |
| 4,627,850 | 12/1986 | Deters et al. | 604/892 |
| 4,693,886 | 9/1987 | Ayer | 604/892.1 |
| 4,781,714 | 11/1988 | Eckenhoff et al. | 604/892.1 |
| 4,842,867 | 6/1989 | Ayer et al. | 604/892.1 |
| 4,929,233 | 5/1990 | Roth et al. | 604/892.1 |

FOREIGN PATENT DOCUMENTS

| 2524311 | 10/1983 | France | 424/453 |
|---|---|---|---|

*Primary Examiner*—C. Fred Rosenbaum
*Assistant Examiner*—Ronald K. Stright, Jr.
*Attorney, Agent, or Firm*—Paul L. Sabatine; Richard T. Ito; Felissa H. Cagan

[57] ABSTRACT

An osmotic system is disclosed for delivering a beneficial agent formulation to an environment of use. The osmotic system comprises (a) an outside semipermeable wall, (b) a middle osmotically active layer, (c) a capsule comprising a beneficial agent, and (d) a passageway for dispensing the beneficial agent from the osmotic system.

2 Claims, 4 Drawing Sheets

OSMOTIC DOSAGE SYSTEM FOR LIQUID DRUG DELIVERY

RELATED APPLICATION

This application is a continuation of U.S. Ser. No. 07/502,705 filed Apr. 2, 1990 now U.S. Pat. No. 5,324,280.

DISCLOSURE OF TECHNICAL FIELD

This invention pertains to an osmotic dosage system. More particularly, the invention relates to an osmotic dosage system comprising means for delivering a liquid drug formulation. Specifically, the osmotic dosage system comprises (1) a wall that surrounds (2) a hydro-activated push layer that surrounds (3) a capsule comprising a liquid drug formulation. The osmotic system comprises at least one orifice that connects the exterior with the interior of the osmotic system for delivering the liquid drug formulation from the osmotic system over time.

DISCLOSURE OF BACKGROUND OF THE INVENTION

Osmotic dosage systems comprising means for delivering a solid drug formulation by displacing physically the solid drug formulation from the osmotic system are known to the prior art in U.S. Pat. No. 4,327,725 issued to Cortese and Theeuwes, and in U.S. Pat. Nos. 4,612,008; 4,765,989; and 4,783,337 issued to Wong, Barclay, Deters and Theeuwes. An osmotic system comprising means for displacing physically a liquid drug formulation from an osmotic system is known to the prior art in U.S. Pat. No. 4,627,850 issued to Deters, Theeuwes, Mullins and Eckenhoff.

The osmotic systems disclosed in these patents mentioned immediately above comprise in at least a part a semipermeable wall that surrounds a compartment. The compartment comprises a drug formulation, and in contact with the drug formulation, a displacement member that pushes the drug formulation from the osmotic system. These osmotic systems operate by imbibing fluid through the semipermeable wall into the compartment, wherein the fluid contacts and motivates the displacement member to consume space and thereby pushes the drug formulation from the osmotic system. These osmotic systems operate successfully for their intended use, and they can deliver many difficult to deliver drugs for their intended purpose. One limitation, however, associated with these osmotic systems consist in the drug formulation being in direct contact with the displacement member as it may be incompatible therewith, while another limitation is that the osmotic system imbibes into the compartment fluid that may be incompatible with the drug formulation.

It will be appreciated, in the light of the above presentation, by those versed in the drug delivery art, that if an osmotic system can be provided that overcomes the limitations associated with the prior art, and exhibits a high level of drug delivery activity, such as osmotic system would have a positive therapeutic value and represent an advancement in the dispensing art. Likewise, it will be immediately appreciated by those versed in dispensing art that if an osmotic system is made available for delivering a liquid drug formulation at a controlled and pharmodynamic osmotic activity, said osmotic system would find practical applications in the fields of pharmacy, human medicine and veterinary medicine.

DISCLOSURE OF OBJECTS OF THE INVENTION

Accordingly, in view of the above presentation, it is an immediate object of this invention to provide an osmotic system that overcomes the limitations associated with the prior art.

Another object of the invention in light of the above presentation, is to provide an osmotic system that can be manufactured by standard manufacturing techniques into osmotic devices of various sizes, shapes and forms that represent a further improvement and advancement in the dispensing art.

Another object of the invention is to provide an osmotic system manufactured in the form of an osmotic device For delivering in vivo a beneficial liquid drug formulation, such as a lipophilic drug formulation, that is difficult to deliver and now can be delivered by the osmotic system provided by this invention in therapeutically effective amounts over time.

Yet another object of the invention is to provide an osmotic system comprising a therapeutic, lipophilic-liquid formulation that initially is essentially-free of direct contact with a hydro-activated expansion composition, and which formulation can be delivered by the osmotic system provided by this invention at a controlled rate and continuously over a prolonged period of time.

Yet still another object of the invention is to provide an osmotic system that comprises a lipophilic, fluid formulation that can be delivered from an osmotic system comprising a hydro-activated layer that surrounds a capsule, and which osmotic system maintains its physical and chemical integrity and is simple in construction, and exhibits all the practical benefits of controlled and continuous administration of the formulation during the osmotic system's residency in a biological environment of use over a prolonged period of time.

Still another object of the invention is to provide an osmotic system for administering a liquid drug formulation to the gastrointestinal tract by the invention making available an osmotic system comprising at least one wall that maintains its integrity in the gastrointestinal tract during its completed transit therethrough.

Yet still another object of the invention is to provide an osmotic system comprising an exterior wall surrounding a middle hydro-activated layer and an inner capsular wall, which inner capsular wall surrounds an internal compartment comprising a liquid drug formulation that can be delivered by the osmotic system at meaningful and useful rates over a prolonged period of time.

Yet still another object of the invention is to provide an osmotic system comprising an exterior wall comprising a semipermeable composition that maintains its integrity and encapsulates a middle layer comprising a hydro-activated swellable composition that swells at a controlled rate or a hydro-activated solute composition that occupies space at a controlled rate, and an inner wall that surrounds a compartment containing a liquid drug formulation.

Yet still another object of the invention is to provide an osmotic system comprising a compartment containing a useful agent formulation and a pharmaceutically acceptable carrier, which compartment is encapsulated by a wall having an osmotic orifice for delivering the useful agent from the osmotic systems over a prolonged period of time up to 24 hours.

Other objects, features, aspects and advantages of the invention will be more apparent to those versed in the art from the following detailed specification taken in conjunction with the drawings and the accompanying claims.

BRIEF DISCLOSURE OF THE DRAWING FIGURES

In the drawing figures, which are not drawn to scale, but are set forth to illustrate various embodiments of the invention, the drawing figures are as follows.

Figure 1:
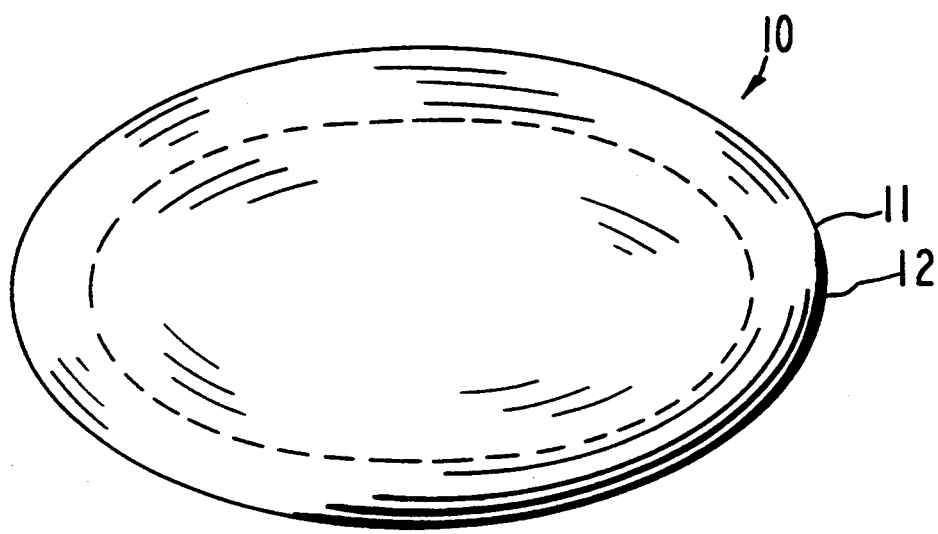
FIG. 1 is a view of an osmotic system provided by the invention for delivering a beneficial agent to an agent receiving environment of use.
Figure 2A:
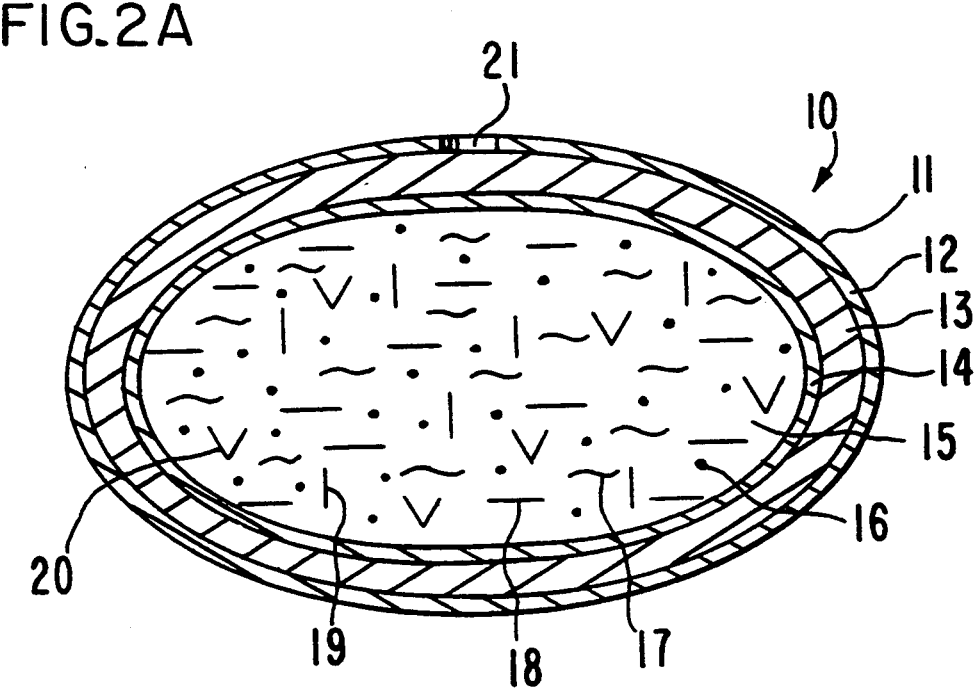
FIG. 2A is an opened view of FIG. 1 illustrating the structure of the osmotic system comprising a sealed capsule enclosing a useful agent formulation.
Figure 2B:
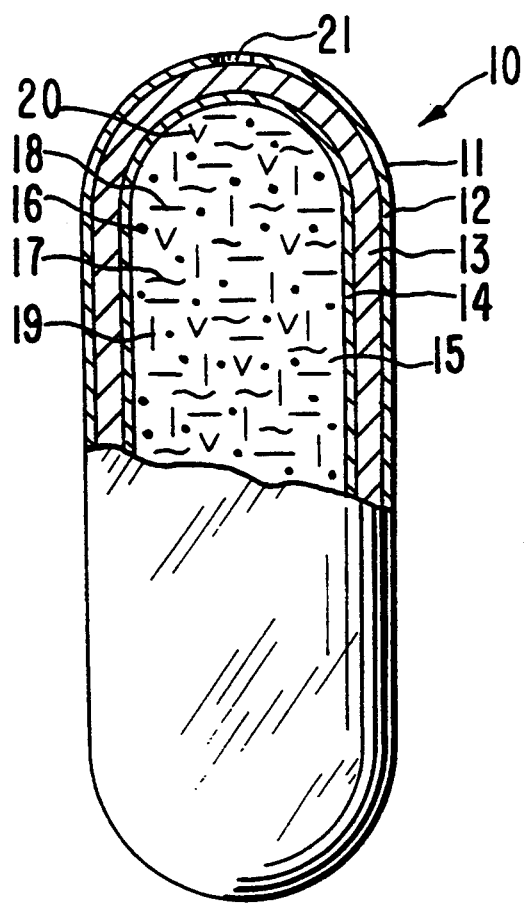
Figure 3A:
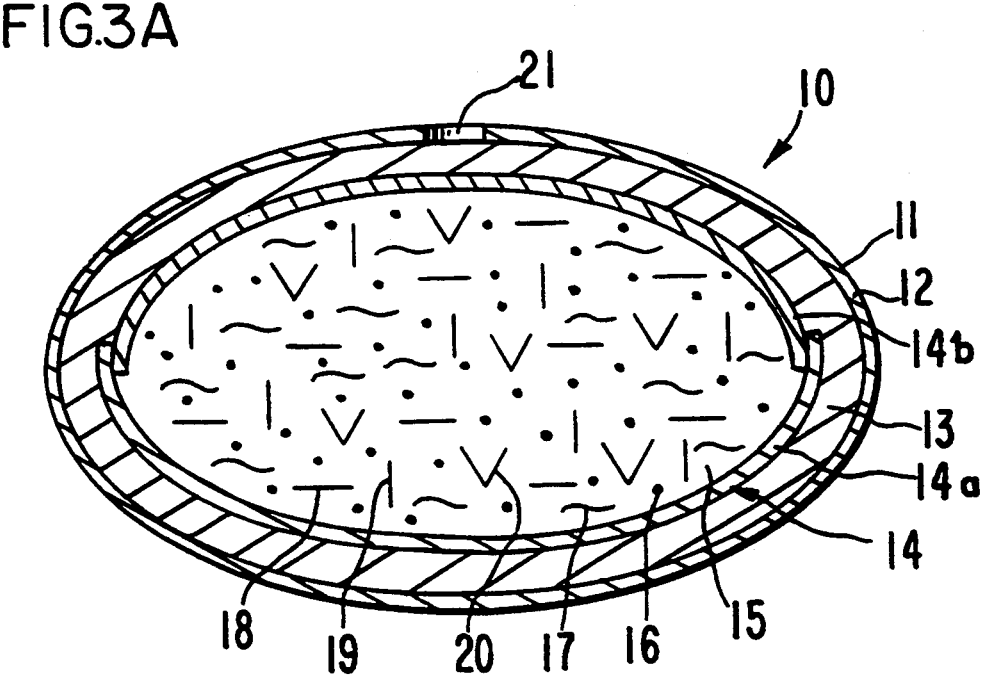
Figure 3B:
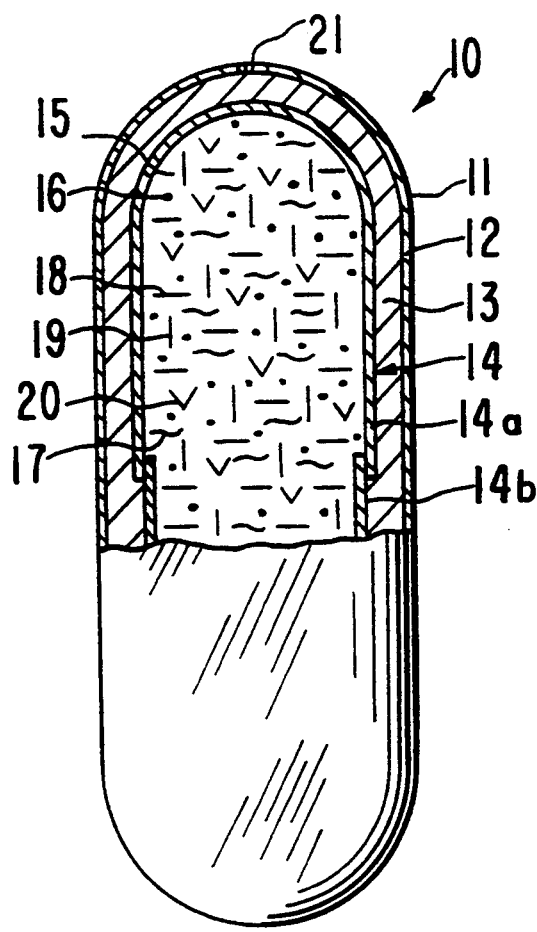
Figure 4:
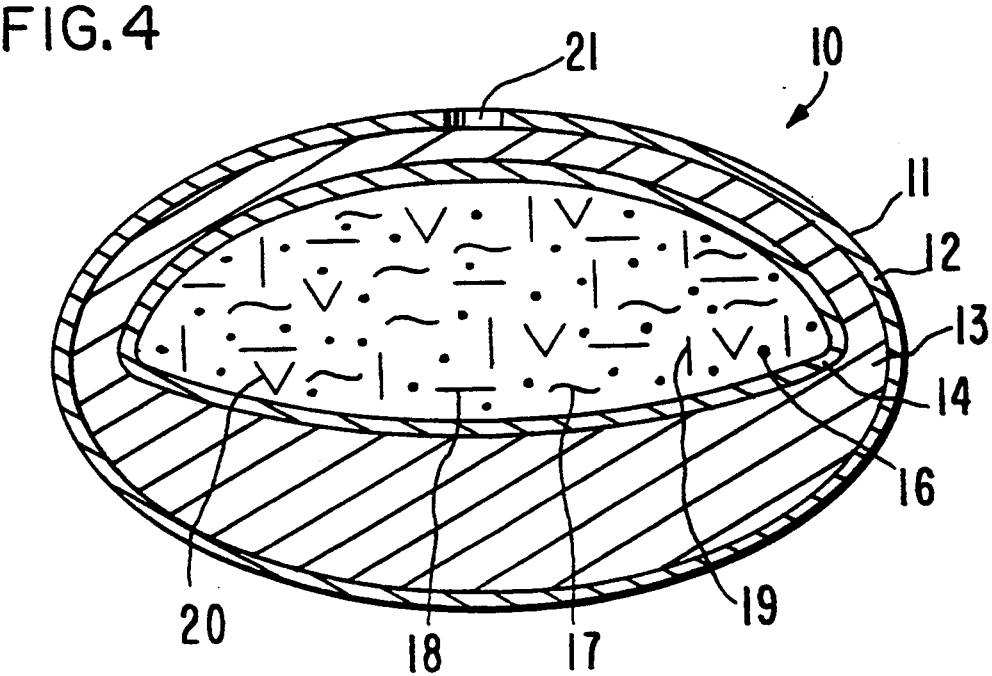
Figure 5:
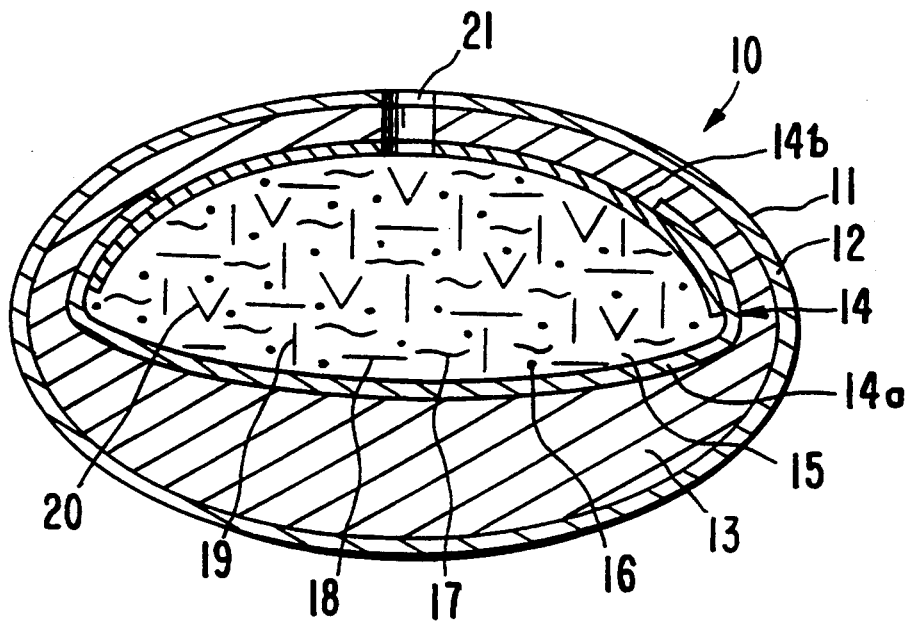
Figure 6:
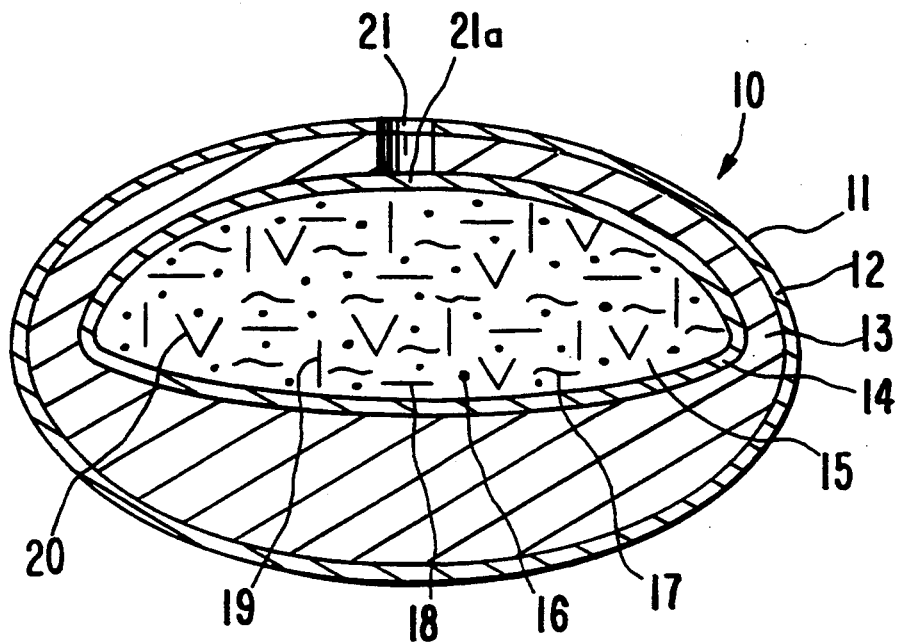

FIG. 2B, seen in partial opened view, depicts another manufacture provided by the invention, wherein the inner capsule is made as a single unit;

FIG. 3A is an opened view of FIG. 1 illustrating the structure of the osmotic system comprising a two piece capsule enclosing a useful agent formulation;

FIG. 3B, seen in partial opened view, depicts another manufacture provided by this invention, wherein the inner capsule is composed of two parts, a cap and a body;

FIG. 4 is an opened view of the osmotic system of FIG. 1 depicting the structure comprising an asymmetrical middle layer encapsulating an inner disposed one piece capsule;

FIGS. 5 and 6 are an opened view of the osmotic system of FIG. 1 depicting the structure of the osmotic system comprising a preformed orifice through the exterior wall and middle layer with the orifice through the inner layer formed during operation of the osmotic systems;

In the drawing figures and in the specification, like parts in related figures are identified by like parts. The terms appearing earlier in the specification and in the description of the drawing figures, as well as embodiments thereof, are further detailed elsewhere in the disclosure.

DETAILED DISCLOSURE OF THE DRAWING FIGURES

Turning now to the drawing figures in detail, which drawing figures are examples of osmotic systems provided by the invention, and which examples are not to be construed as limiting, one example of an osmotic system is seen in drawing FIG. 1. In FIG. 1, an osmotic system 10 is seen comprising a body member 11 comprising a wall 12, that surrounds an internal structure not seen in FIG. 1.

In FIG. 2A, osmotic system 10 comprises a body 11, comprising a wall 12 that surrounds a hydro-activated layer 13 and an inner capsule 14. Internal capsule 14 completely surrounds and capsulates an internal compartment 15. In drawing FIG. 2A, wall 12 comprises totally a semipermeable composition, or wall 12 comprises at least in part a semipermeable composition permeable to the passage of fluid and essentially impermeable to the passage of drugs and osmotic solvents. When wall 12 comprises in at least a part a semipermeable composition, the remainder of wall 12 is comprised of a non-semipermeable composition. Further in drawing FIG. 2A, hydro-activated layer 13 comprises in one embodiment an osmotic composition comprising an osmotic solute that exhibits an osmotic pressure gradient across semipermeable wall 12 against an external fluid present in the environment of use. In another embodiment, hydro-activated layer 13 comprises a hydrogel that imbibes and/or absorbs fluid into layer 13 through outer semipermeable wall 12. Semipermeable wall 12 is non-toxic, it maintains its physical and chemical integrity during the operation of osmotic system 10 and it is essentially free of interaction with hydro-activated layer 13. Further in FIG. 2A, inner capsule 14 is made in its final manufacture as a single unit capsule. That is, capsule wall 14 cannot be separated into its original parts.

Compartment 15 of osmotic dosage system 10 comprises an effective amount of a therapeutic agent 16, represented by dots, and in a presently preferred embodiment, a pharmaceutically acceptable carrier 17 for therapeutic agent 16, represented by wavy lines. Compartment 15 optionally comprises other dosage-forming ingredients, such as an anti-oxidant 18 represented by dashes, a suspending agent 19 represented by vertical dashes, a surface active agent 20 represented by V, and the like compartment 15 comprises, in one presently preferred embodiment a hydrophobic, lipophilic drug composition for producing an intended result in a biological environment. Compartment 15 releases a drug composition through at least one passageway 21 to an environment if use.

Drawing FIG. 2B depicts an inner capsule 14 manufactured as a single body unit comprising the standard capsule shape. In the embodiment illustrated in FIG. 2B, the inner capsule can be divided into sizes (000), (00), (0), (1), (2), (3), (4), and (5), wherein the diameter of the capsule is within the range of 6 mm to 3.0 mm. The inner capsule 14 with the largest number has the smallest size. These capsules are disclosed in *Microcapsule Processing and Technology,* by Kondo and Van Vackenburg, page 2, (1979) published by Marcel Dekker, Inc., New York.

Drawing FIG. 3A, seen in cross-section, depicts another osmotic dosage form 10 as provided by the invention. In FIG. 3A, dosage form 10 comprises a body 11, an outside wall 12 and a hydroactivated layer 13. In the osmotic dosage form illustrated in drawing FIG. 3, the inner capsule wall 14 is made conveniently in two parts, with one part 14a slipping over and capping the other part 14b. The two parts completely surround and capsulate the internal lumen or compartment 15. Compartment 15 comprises a beneficial agent 16, a pharmaceutically acceptable carrier 17, an optional antioxidant 18, an optional suspending agent 19, and an optional surfactant 20.

Drawing FIG. 3B depicts an inner capsule 14 manufactured in the standard shape. The inner capsule 14 comprises two parts, a cap 14a that slips over a body 14b. The two parts are fitted together after the body 14b is filled with a preselected formulation. The assembly is done by slipping or telescoping the cap section over the body section, thereby completely surrounding and encapsulating the formulation. Capsules comprising a standard configuration are known in *Pharmaceutical Sciences,* by Remington, 14th Ed., pp 1671 to 1677, (1970) published by Mack Publishing Co., Easton, Pa.

The osmotic dosage system as seen in drawing FIGS. 2A and 2B and in drawing FIGS. 3A and 3B depicts internal capsule walls possessing two distinct forms, classified for the purpose of this invention, a soft capsule 14 as seen in FIG. 2A and 2B, and a hard capsule 14 as seen in FIGS. 3A and 3B. The soft capsule, as used by the present invention, preferably in its final form, comprises one piece. Generally, the soft capsule 14 is of sealed construction encapsulating a useful agent formulation therein. The soft capsule is made by various processes including the plate process, the rotary die process, the reciprocating die process, and the continuous process. The plate process uses a set of molds. A warm sheet of a prepared capsule-wall forming material is laid over a lower mold and the agent formulation poured on it. A second sheet of wall-forming material is placed over the agent formulation followed by the top mold. The mold is placed under a press and a pressure applied, with or without heat to form a unit, soft capsule member. The capsules are washed with a solvent for removing excess agent formulation from the exterior of the capsule, and the air-dried capsule is capsuled with a layer of a hydro-activated compensation.

A hard capsule 14 is composed of two parts, a cap and a body, which are fitted together after the larger body is filled with a preselected appropriate agent formulation. This is done by slipping or telescoping the cap section over the body section, thus completely surrounding and encapsulating the useful agent formulation. A hard capsule 14 is made by dipping stainless steel molds into a bath containing solution of a capsule wall-forming material to coat the mold with the material. Then, the molds are withdrawn, cooled, and dried in a current of air. The capsule is stripped from the mold and trimmed to yield the capsule with an internal lumen. The engaging caps that telescopically caps the agent formulation receiving body is made in a similar manner. Then, the closed and filled capsule is capsulated with a layer of a hydro-activated composition and an outer semipermeable wall. In another embodiment, the hard capsule can be made with each part having, matched locked rings near the opened end that permits joining and locking together the overlapping cap and body after filling with agent formulation. In this embodiment, a pan of matched locking rings are formed into the cap portion and the body portion, and these rings provide the locking means for security holding together the capsule. The capsule can be manually filled with the agent formulation, or they can be machine filled with the agent formulation. In the final manufacture, the hard capsule is capsuled with a contacting layer of a hydro-activated composition and then with a semipermeable wall permeable to the passage of fluid and substantially impermeable to the passage of useful agent and osmotic solutes.

The rotary die process for providing a capsule comprises two continuous films of capsule wall-forming materials that are brought into convergence between a pan of revolving dies and an injector wedge. The process fills and seals the capsule in dual and coincident operations. In this process, the sheets of capsule wall-forming compositions are fed over guide rolls, and then down between the wedge injector and the die rolls. The agent formulation to be capsulated flows by gravity into a positive displacement pump. The pump meters the agent formulation through the wedge injector and into the sheets between the die rolls. The bottom of the wedge contains small orifices lined-up with the die pickets of the die rolls. The capsule is about half-sealed when the pressure of pumped agent formulation forces the sheets into the die pockets. Wherein the soft capsules are simultaneously filled, shaped, hermetically sealed and cut from the sheets of wall-forming compositions. The sealing of the soft capsule is achieved by mechanical pressure on the die rolls and by heating the sheets of wall-forming composition by the wedge. After manufacture, the agent formulation-filled capsules are dried in the presence of forced air, and a hydro-activated layer and a semipermeable wall capsuled thereto, by processes described hereafter.

The reciprocating die process produces soft capsules by leading two films of capsule wall-forming compositions between a set of vertical dies. The dies as they close, open, and close perform as a continuous vertical plate forming row after row of pockets across the film. The pockets are filled with agent formulation, and as the pockets move through the dies, they are sealed, shaped and cut from the moving film as capsules filled with agent formulation. A hydro-activated layer and a semipermeable wall is coated thereon to yield the osmotic dosage system. The continuous process is a manufacturing system that also uses rotary dies with the added feature that the process can successfully fill active agent into a soft capsule, to encapsulating liquids therein. The filled soft capsule of the continuous process is encapsulated with both the hydro-activated layer and a semipermeable polymeric composition to yield the inner soft capsule.

Drawing FIG. 4, seen in opened-section depicts another osmotic dosage system 10 as provided by in the invention. In Figure 4, dosage form 10 comprises a body 11, an outside wall 12, a hydroactivated layer 13, and an inner capsule wall 14. The capsule wall 14 surrounds an inner compartment 15. Compartment 15 comprises a beneficial agent 16, a pharmaceutically acceptable carrier 17, an anti-oxidant 18, a suspending agent 19 and a surface active agent 20. A composition, in one example, comprising a beneficial agent and a pharmaceutically acceptable carrier can exhibit a viscosity of $10^{-1}$ to $10^{-7}$ poises, and the like. In osmotic dosage system 10, inner capsule wall 14 is of single unit construction and it is surrounded by an unsymmetrical hydro-activated layer 13. As hydro-activate layer 13 imbibes and/or absorbs external fluid, it expands and applies a push pressure against wall 13 for pushing agent 16 through passageway 21. The presence of the unsymmetrical layer 13 functions to assure that the maximum dose of agent 16 is delivered from system 10, as the broader section of layer 13 distant from passageway 21 swells and moves towards passageway 21.

Drawing FIG. 5 depicts dosage system 10 in opened section, which figure illustrates a body 11, an outside wall 12, a hydro-activated layer 13, and an inner capsule wall 14. The capsule wall 14 surrounds an inner compartment 15. Compartment 15 comprises a beneficial agent 16, a pharmaceutically acceptable carrier 17, an anti-oxidant 18, a suspending agent 19, and a surface active agent 20 in this example, inner capsule 14 is a two piece capsule comprising capsule members 14a and 14b. The hydro-activated layer 13 is unsymmetrical in this manufacture to effect maximum delivery of agent 16 through passageway 21.

Drawing FIG. 6 depicts a dosage system 10 in opened section for illustrating a body 11, an outside wall 12, a hydro-activated layer 13, an inner capsule wall 14, a compartment 15 comprising a beneficial agent 16, a pharmaceutically acceptable carrier 17, an anti-oxidant 18, a suspending agent 19, and a surface active agent 20. In the dosage system illustrated, a passageway comprises a preformed passageway 21 through outside wall 12 and hydro-activated layer 13, and a passageway 21a through capsule wall 14, which passageway 21a is formed during operation of osmotic dosage form 10.

While drawing FIGS. 1 through 6 are illustrative of various osmotic systems that can be provided according to the invention, it is to be understood these devices are not be construed as limiting, as these osmotic systems can take a wide variety of shapes, sizes and forms adapted for delivering a beneficial agent to the environment of use. For example, the osmotic systems comprise buccal, implant, anal, artificial gland, cervical, intrauterine, ear, nose, dermal, vaginal, percutaneous, subcutaneous, and like delivery systems. The pharmaceutical applications of the dosage system embraces ethical and proprietary products for human and veterinary use. The osmotic system can be used also for packaging and delivering breath fresheners, perfumes, bath oils containing dermal medicaments, bubble baths containing therapeutics and the like. The osmotic system also can be sized, shaped, structured and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, clinical reactions, and other environments of use.

DETAILED DISCLOSURE OF THE INVENTION

In accordance with the practice of this invention, it has now been found that osmotic system 10 can be provided with a semipermeable wall 12 comprising a composition that does not adversely affect the host, the beneficial agent, an osmopolymer, an osmogent, and the like. The semipermeable wall is permeable to the passage of an external fluid such as water and biological fluids, and it is substantially impermeable to the passage of a beneficial agent, an osmogent, an osmopolymer, and the like. The selectively semipermeable compositions used for forming wall 12 are essentially non-erodible and they. are insoluble in biological fluids during the life of the osmotic system.

Representative polymers for forming wall 12 comprise semipermeable homopolymers, semipermeable copolymers, and the like. In one presently preferred embodiment, the compositions comprise cellulose esters, cellulose ethers, and cellulose ester-ethers. The cellulosic polymers have a degree of substitution, D.S. on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkylsulfamate, semipermeable polymer forming groups, and the like.

The semipermeable compositions typically include a member selected from the group consisting of cellulose acylate, cellulose diacylate, cellulose triacylate, cellulose triacetate, cellulose acetate, cellulose diacetate, cellulose triacetate, mono-, di- and tri-cellulose alkanylates, mono-, di-, and tri-alkenylates, mono-, di-, and tri-aroylates, and the like. Exemplary polymers include cellulose acetate have a D.S. of 1.8 to 2.3 and an acetyl content of 32 to 39.9%; cellulose diacetate having a D.S. of 1 to 2 and an acetyl content of 21 to 35%, cellulose triacetate having a D.S. of 2 to 3 and an acetyl content of 34 to 44.8%, and the like. More specific cellulosic polymers include cellulose propionate having a D.S. of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 4.7%; cellulose triacylates having a D.S. of 2.6 to 3 such as cellulose trivalerate, cellulose trilamate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate, and the like; mixed cellulose esters such as cellulose acetate valerate, cellulose acetate succinate, cellulose propionate succinate, cellulose acetate octanoate, cellulose valerate palmitate, cellulose acetate heptonate, and the like. Semipermeable polymers are known in U.S. Pat. No. 4,077,407 and they can be synthesized by procedures described in *Encyclopedia of Polymer Science and Technology*, Vol. 3, pages 325 to 354, 1964, published by Interscience Publishers, Inc., New York.

Additional semipermeable polymers for forming wall 12 comprise cellulose acetaldehyde dimethyl acetate.; cellulose acetate ethylcarbamate; cellulose acetate methyl carbamate; cellulose dimethylaminoacetate; semipermeable polyamide; semipermeable polyurethanes; semipermeable sulfonated polystyrenes; cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb et al. in U.S. Pat. No. 3,133,132; semipermeable polystyrene derivatives; semipermeable poly (sodium styrenesulfonate); semipermeable poly (vinylbenzyltremethylammonium chloride); semipermeable polymers, exhibiting a fluid permeability of $10^{-5}$ to $10^{-2}$ (cc. mil/cm hr.atm) expressed as per atmosphere of hydrostatic or osmotic pressure differences across a semipermeable wall. The polymers are known to the art in U.S. Pat. Nos. 3,845,770; 3,916,899; and 4,160,020; and in *Handbook of Common Polymers*, by Scott, J. R., and Roff, W. J., 1971, published by CRC Press, Cleveland, Ohio.

The hydro-activated layer 13 in one preferred embodiment comprises hydrogels also known as osmopolymers. The osmopolymers exhibit fluid inbibition properties. The osmopolymers are swellable, hydrophilic polymers, which osmopolymers interact with water and biological aqueous fluids and swell or expand to an equilibrium state. The osmopolymers exhibit the ability to swell in water and biological fluids and retain a significant portion of the imbibed fluid within the polymer structure. The osmopolymers swell or expand to a very high degree, usually exhibiting a 2 to 50 fold volume increase. The osmopolymers can be noncross-linked or cross-linked. The swellable, hydrophilic polymers are in one presently preferred embodiment lightly cross-linked, such cross-links being formed by covalent or ionic bonds or residue crystalline regions after swelling. The osmopolymers can be of plant, animal or synthetic origin. The osmopolymers are hydrophilic polymers. Hydrophilic polymers suitable for the present purpose include poly (hydroxy-alkyl methacrylate) having a molecular weight of from 30,000 to 5,000,000; poly (vinylpyrrolidone) having a molecular weight of from 10,000 to 360,000; anionic and cationic hydrogels; polyelectrolytes complexes; poly (vinyl alcohol) having a low acetate residual, cross-linked with glyoxal, formaldehyde, or glutaraldehyde and having a degree of polymerization of from 200 to 30,000; a mixture of methyl cellulose, cross-linked agar and carboxymethyl cellulose; a mixture of hydroxypropyl methylcellulose and sodium carboxymethylcellulose; a mixture of hydroxypropyl ethylcellulose and sodium carboxymethyl cellulose; sodium carboxymethylcellulose; potassium carboxymethylcellulose; a water insoluble, water swellable copolymer formed from a dispersion of finely divided copolymer of maleic anhydride with styrene, ethylene, propylene, butylene or isobutylene cross-linked with from 0.001 to about 0.5 moles of saturated cross-linking agent per mole of maleic anhydride per copolymer; water swellable polymers of N-vinyl lactams; polyoxyethylene-polyoxypropylene gel; polyoxybutylene-polyethylene block copolymer gel; carob gum; polyacrylic gel; polyester gel; polyuria gel; polyether gel; polyamide gel; polycellulosic gel; polygum gel; initially dry hydrogels that imbibe and absorb water which penetrates the glassy hydrogel and lowers its glass temperature; and the like.

Representative of other osmopolymers comprise polymers that form hydrogels such as Carbopol ® acidic carboxypolymer, a polymer of acrylic and cross-linked with a polyallyl sucrose, also known as carboxypolymethylene and carboxyvinyl polymer having a molecular weight of 250,000 to 4,000,000; Cyanamer ® polyacrylamides; cross-linked water swellable indene-maleic anhydride polymers; Good-rite ® polyacrylic acid having a molecular weight of 80,000 to 200,000; Polyox ® polyethylene oxide polymer having a molecular weight of 100,000 to 5,000,000 and higher; starch graft copolymers; Aqua-Keeps ® acrylate polymer polysaccharides composed of condensed glucose units such as diester cross-linked polygluran; and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; and in *Handbook of Common Polymers,* by Scott and Roff, published by the Chemical Rubber Co., Cleveland, Ohio. The amount of osmopolymer comprising hydro-activated layer is from 5% to 100%.

The hydro-activated layer in another manufacture comprises an osmotically effective compound that comprises inorganic and organic compounds that exhibit an osmotic pressure gradient across a semipermeable wall against an external fluid. The osmotically effective compounds, as with the osmopolymers, imbibe fluid into the osmotic system, thereby making available fluid to push against the inner wall 14 for pushing beneficial agent 16 from osmotic system 10. The osmotically effective compounds are known also as osmotically effective solutes, and also as osmagents. Osmotically effective solutes used for forming hydro-activated layer 13 comprise magnesium sulfate, magnesium chloride, potassium sulfate, sodium sulfate, lithium sulfate, potassium acid phosphate, mannitol, urea, inositol, magnesium succinate, tartaric acid, carbohydrates such as raffinose, sucrose, glucose, lactose, sorbitol, and mixtures therefor. The amount of osmagent in layer 13 is from 5% to 100%. Layer 13 optionally comprises an osmopolymer and an osmagent with the total amount of osmopolymer and osmagent equal to 100%. Osmotically effective solutes are known to the prior art in U.S. Pat. No. 4,783,337.

Inner capsule 14 comprises capsule forming compositions comprising gelatin, gelatin having a viscosity of 15 to 30 millipoises and a bloom strength up to 150 grams; gelatin having a bloom value of 160 to 250; a composition comprising gelatin, glycerine, water and titanium dioxide; a composition comprising gelatin, erythrosin, iron oxide and titanium dioxide; a composition comprising gelatin, glycerine, sorbitol, potassium sorbate and titanium dioxide; a composition comprising gelatin, acacia glycerine, and water; and the like. Materials useful for forming capsule wall are known in U.S. Pat. Nos. 4,627,850; and in 4,663,148.

A piasticizer is compounded in a preferred embodiment with wall 12 or wall 14 for increasing the flow prospects and for enhancing the workability of the polymer during manufacture of the respective outer or inner wall. For example, glycerin can be used for plasticizing gelatin, pectin, casein or polyvinyl alcohol. Other plasticizers that can be used for the present purpose compare triethyl citrate, diethyl phthalate, diethyl sebacate and the like. The amount of plasticizer when present is from 0.05 to 30% of the weight of the composition.

The expression "passageway" as used herein comprises means and methods suitable For releasing the beneficial agent from the osmotic system. The expression includes aperture, orifice, hole, bore, pore, orous element, orous overlay, porous insert, hollow fiber, capillary tube, microporous insert, microporous overlay, and the like. The passageway can be formed by mechanical drilling, laser drilling, eroding an erodible element, extracting, dissolving, bursting, or leaching a passageway former from the wall. The passageway can be a pore formed by leaching sorbitol, lactose or the like from a wall or layer as disclosed in U.S. Pat. No. 4,200,098. This patent discloses pores of controlled-size porosity formed by dissolving, extracting, or leaching a material from a wall, such as sorbitol from cellulose acetate. The pore-passageways extend from the inside to the outside of a wall or layer for effective release of beneficial agent including a drug to the exterior of the osmotic system. U.S. Pat. No. 4,285,987 discloses an osmotic system comprising a first osmotic system comprising a cellulose acetate wall comprising leachable sorbitol for forming a pore for releasing an osmotically active beneficial agent from an osmotic core. This patent, discloses an osmotic system that exhibits drug released through a pore-passageway and drug released through a laser-drilled passageway within the total structure of the same osmotic system. A passageway can extend through wall 12, inner composition 13 and inner wall 14 as seen in FIG. 3A or the passageway initially extends through wall 12, with the passageway on composition 13 and inner wall 14 forming in the environment of use as seen in FIG. 2A. Passageways are known also in U.S. Pat. No. 4,783,337.

The expression "active agent" as used herein, comprises any beneficial agent, therapeutic compound, or composition that can be delivered from the osmotic system to produce a beneficial and useful result. The term beneficial agent also includes algicide, antioxidant, air purifier, biocide, bactericide, catalyst, chemical reactant, disinfectant, fungicide, fermentation agent, fertility inhibitor, fertility promotor, germicide, plant growth promotor, plant growth inhibitor, preservative, rodenticide, sterilization agent, sex sterilant for insects, and the like.

In the specification and in the accompanying claims, the term beneficiai agent also includes drugs. The term drug includes any physiologically or pharmacologically active substance that produces a local or a systemic effect, in animals, including warm-blooded mammals, humans and primates; avians; household, sport, and farm animals; laboratory animals; fishes; reptiles; and zoo animals. The term "physiologically" as used herein, generically denotes the administration of a drug to produce generally normal drug levels and functions. The term "pharmacologically" denotes generally variations in response to the amount of drug administered to a host. The drug can be in various forms such as unchanged molecules, molecular complexes, pharmacologically acceptable salts such as hydrochloride, hydrobromide, sulfate, laurate, palmitate, phosphate, nitrite, nitrate, borate, acetate, maleate, tartiate, oleate, salicylate, and the like. For acidic drugs, salts of metals, amines, or organic cations, for example quarternary ammonium can be used. Derivatives of drugs, such as bases, ester, ether and amide can be used. A drug that is water insoluble can be used in a form that is water soluble derivative thereof, or as a base derivative thereof, which in either instance on its delivery by the osmotic system, is converted by enzymes, hydrolyzed by the body pH, or by other metabolic processes to the original therapeutically active form. The expression "drug formulation" indicates the drug present in a preferred embodiment in the osmotic system accompanied by a binder, antioxidant, pharmaceutically acceptable carrier, and the like. The amount of a beneficial agent in an osmotic system generally is about 0.05 ng to 5 g or more, with individual osmotic devices comprising, for example, 25 ng, 1 mg, 5 mg, 10 mg, 25 mg, 125 mg, 250 mg, 500 mg, 750 mg, 1.0 g, 1.2 g, 1.5 g, and the like. The osmotic system can be administered once, twice or thrice daily.

The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synoptic sites, neuroeffector junctional sites, endocrine system, hormone systems, immunological system. organ systems, reproductive system. skeletal system, autocoid systems, alimentary and excretory systems, inhibitory of autocoids and histamine systems, and physiological systems. The active drug that can delivered for acting on these animal systems includes depressants, beta-blockers, hypnotics, sedatives, psychic energizers, tranquilizers, anti-convulsants, muscle relaxants, steroids, antiparkinson agents, analgesics, anti-inflammatories, polypeptides, local anesthetics, muscle contractants, anti-microbials, anti-malarials, hormonal agents, contraceptives, sympathomimetics, diuretics, anti-parasitics, neoplastics, hypoglycemics, ophthalmics, electrolytes, diagnostic agents, cardiovascular drugs, calcium channel blockers, angiotensin-converting enzyme inhibitors, and the like.

Exemplary drugs that can be delivered by the osmotic system of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metroprolol tartrate, cimetidine hydrochloride, diphenidol, meclizine hydrochloride, prochlorperazine maleate, phenoxybenzamine, thiethylperazine, maleate, anisindone, diphenadione erythrityl teranitrate, dizoxin, isofurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, estrogenic progrestational, corticosteriods, hydrocortisone, hydrocorticosterone acetate, cortisone acetate, triamcinolone, methyltesterone, $17\beta$-estradiol, ethinyl estradiol, ethinyl estradiol 3-methyl ether, prednisolone, 17-hydroxyprogesterone acetate, 19-nor-progesterone, norgestrel, norethindone, norethiderone, progesterone, norgestrone, orethynodrei, aspirin, indomethacin. naproxen, fenoprofen, sulidac. diclofenac, indoprofen, nitroglycerin, propranolol, metroprolol, valproate, oxprenolol, timolol, atenolol, alprenolol, cimetidine, clonidine, imipramine, levodopa, chloropropmazine, resperine, methyldopa, dihydroxyphenylalanine, pivaloyloxyethyl ester of $\epsilon$-methyldopa hydrochloride, theophylline, calcium gluconate ferrous lactate, ketoprofen, ibuprofen, cephalexin, erythromycin, haloperiodol, zomepirac, vincamine, diazepam, phenoxybenzamine, $\beta$-blocking agents, calcium-channel blocking drugs such as nifedipine, diltiazen, verapami l, and the like.

The drug includes angiotension-converting enzyme inhibitors such as 1 isinopril, captopril, ramipril, fosimopril, benazepril, libenzapril, cilazapril cilazaprilat, perindopril, zofenopril, enalapril, imidapril, spirapril, rentiapril, delapril, alindapril, indalapril, qumapril, and the like. The beneficial drugs are known to the dispensing art in *Pharmaceutical Sciences*, edited by Remington 14th Ed., 1979, published by Mark Publishing Co., Easton, Pa.; *The Drug, The Nurse, The Patient, Including Current Drug Handbook*, 1976, by Falconer et al., published by Saunder Company, Philadelphia, Pa.; *Medical Chemistry*, 3rd Ed., Vol 1 and 2, by Burger, published by Wiley-Interscience, New York; and, *Physician's Desk Reference*, 43 Ed, 1989, published by Michael Economics Co., New Jersey.

The pharmaceutically acceptable carrier useful for mixing with a drug to provide a dispensable formulation, in a presently preferred embodiment, are carriers that are easily excreted, metabolized, assimilated, or the like by a warm-blooded animal. The carrier medium used for the present purpose can be inorganic, or organic, and of naturally occurring or synthetic origin. Examples of carriers included in the term are substances such as solutions, suspensions, liquids, immiscible liquids, emulsions, sols, colloids, and oils. Representative carriers include liquid alkylene glycols such as ethylene glycol, diethylene glycol, triethylene glycol, ethylene glycol monomethyl ether, liquid polyethylene glycols having a molecular weight of 200, 300, 400 and higher; oils of plant, animal and marine origin such as corn oil almond oil, babassu oil eucalyptus oil, cottonseed oil, palm oil, peanut oil, tung oil, mint oil, whale oil, herring oil, mineral oil, and the like: emulsions of castor oil in aqueous solutions of pigskin gelatin: emulsions of gum arabic, water and ethyl cellulose; liquid glyceryl triesters of a low molecular weight fatty acid; oils with emulsifiers such as mono- or di-glyceride of a fatty acid; a mixture of from about 70% to about 99.9% propylene glycol and from about 0.1% to 30% of glycerin; a mixture of from about .70% to about 99.9% propylene glycol and from about 0.1 to 30% of ethanol; a mixture by volume of from about 80% to 99.9% of propylene glycol and from about 0.1% to about 20% of a mixture of from about 50% to 99.9% of ethanol or glycerin and from 0.1% to about 50% of sterile water; 5% dextrose in physiological saline; oils mixed with poly-oxyethylene sorbitan monolaurate; a mixture of peanut oil and beeswax; peanut oil containing pectin; glycerine and gelatin, with or without added water; glycerincastile soap formulation; distilled monoglycerides, distilled propylene glycol monoesters, succinylated monoglycerides, acetylated monoglycerides, glyceryl monostearates, monoglycerides water-in-oil emulsions having a hydrophilic-lipophilic balance of 4, hydrogenated palm oil, hydrogenated palm oil stearine, hydrogenated soybean oil, hydrogenated vegetable oil, hydrogenated cottonseed oil, partially hydrogenated oils, cottonseed oil, sunflower oil, rapeseed oil, and the like.

Osmotic system 10 in a preferred embodiment comprises an antioxidant in lumen 15, which antioxidant slows or effectively stops the rate of any autoxidizable material present in lumen 15. Representative antioxidants comprises a member selected from the group consisting of ascorbic acid; alpha tocopherol; ascorbyl palmitate; ascorbates; isoascorbates; butylated hydroxyanisole; butylated hydroxytoluene; nordihydroguiaretic acid; esters of garlic acid comprising at least 3 carbon atoms comprising a member selected from the group consisting of propyl gallate, octyl gallate, decyl gallate, decyl gallate: 6-ethoxy-2,2,4-trimethyl-1,2-dihydroguinoline: N-acetyl-2, 6-diol-butyl-p-aminophenol butyl tyrosine; 3-tertiarybutyl-4-hydroxyanisole; 2-tertiary-butyl-4-hydroxyanisole; 4-chloro-2,6ditertiary butylphenol; 2,6-ditertiary butyl p-methoxy phenol; 2,6-ditertiary butyl-p-cresol; polymeric antioxidants; trihydroxybutyro-phenone; physiologically acceptable salts of ascorbic acid, erythorbic acid, and ascorbyl acetate; calcium ascorbate; sodium ascorbate; sodium bisulfite; and the like. The amount of antioxidant used for the present purposes is about 0.001% to 25% of the total weight of the composition present in the lumen 15. Antioxidants are known to the prior art in U.S. Pat. Nos. 2,707,154; 3,573,936; 3,637,772; 4,038,434; 4,186,465; and 4,559,237.

Osmotic system 10, in another preferred embodiment, comprises a surfactant selected from the group consisting of nonionic, anionic and cationic surfactants. Exemplary nontoxic, nonionic surfactants suitable for forming a composition comprise alkylated aryl polyether alcohols known as Triton ®; polyethylene glycol tert-dodecyl throether available as Nonic ®; fatty and amide condensate or Alrosol ®; aromatic polyglycol ether condensate or Neutronyx ®; fatty acid alkanolamine or Ninol ®; sorbitan monolaurate or Span ®; polyoxyethylene sorbitan esters or Tweens ®; sorbitan monolaurate polyoxyethylene or Tween 20 ®; sorbitan mono-oleate polyoxyethylene or Tween 80 ®; poloxypropylene-polyoxyethylene or Pluronic ®; and polyoxypropylene-polyoxyethylene 8500 or Pluronic ®. By way of example, anionic surfactants comprise sulfonic acids and the salts of sulfonated esters such as sodium lauryl sulfate, sodium sulfoethyl oleate, dioctyl sodium sulfasuccinate, cetyl sulfate sodium, myristyl sulfate sodium; sulfated esters; sulfated amides; sulfated alcohols; sulfated ethers; sulfated carboxylic acids; sulfonated aromatic hydrocarbons; sulfonated ethers; and the like. The cationic surface active agents comprise cetyl pyridinium chloride; cetyl trimethyl ammonium bromide; diethylmethyl cetyl ammonium chloride; benzalkonium chloride; benzethonium chloride; primary alkylamonium salts; secondary alkylamonium salts; tertiary alkyl ammonium salts; quaternary alkylamonium salts; acylated polyamines; salts of heterocyclic amines; and the like. Generally, from 0.01 part to 1000 parts by weight of surfactant, per 100 parts of drugs is admixed with the drug to provide the drug formulation. Surfactants are known to the prior art in U.S. Pat. Nos. 2,805,977; and in 4,182,330.

A hydro-activated layer, and a semipermeable wall can be applied to the exterior surface of the capsule by molding, forming, spraying, dipping or the like the capsule into a hydro-activated layer forming composition, or a semipermeable wall forming composition. Another and presently preferred technique that can be used for applying the layer or the wall is the air suspension procedure. This procedure consists in suspending and tumbling the respective compositions in a current of air until the layer or the wall surrounds and coats the capsule. The procedure is repeated with different layer or wall forming composition to form a laminated wall, hydro-activated layer on the capsule. The air suspension procedure is described in U.S. Pat. No. 2,799,241; *J. Am. Pharm. Assoc.,* Vol. 48, pp 451–59, 1979; and ibid, Vol. 49, pp 82–84, 1960. Other standard manufacturing procedures are described in *Modern Plastic Encyclopedia,* Vol. 46, pp 62–70, 1969; and in *Pharmaceutical Sciences,* by Remington 14th Ed., pp 1626–78, 1970, published by Mack Publishing Co., Easton, Pa.

Exemplary solvents suitable for manufacturing the hydroactivated layer and the wall comprise inert inorganic and organic solvents that do not adversely harm the materials, the capsule, and the final laminated wall hydro-activated layer. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride nitroethane, nitropropane tetrachloroethane, ethyl ether, isopropyl ether, cyclohexane. cyclooctane, benzene, toluene, naphtha, 1,4-dioxane, tetrahydrofuran, diglyme, water, aqueous solvents containing inorganic salts such as sodium chloride, calcium chloride, and the like, and mixture thereof such as acetone and water, acetone and methanol, acetone and ethyl alcohol, methylene dichloride and methanol, and ethylene dichloride and methanol.

DETAILED DISCLOSURE OF MODES OF PERFORMING THE INVENTION

The following examples are merely illustrative of the present invention, and they should not be considered as limiting the scope of the invention in any ways, as these examples and other equivalents thereof will become more apparent to those versed in the art in the light of the present disclosure, the drawing figures and the accompanying claims.

EXAMPLE 1

An osmotic system for the controlled delivery of vitamin E is prepared as follows: first, a pharmaceutically acceptable soft capsule comprising a wall about 0.4 mm thick formed of a composition comprising gelatin, glycerine and water surrounds an internal lumen comprising vitamin E. Next, an osmotic forming layer composition comprising sodium carboxymethylcellulose, water and ethanol is coated onto the exterior wall of the soft gelatin capsule. The osmotic coated capsule is dried at room temperature about 25° C. in a current of air to evaporate the wall-forming solvent. The osmotic layer exhibits a dry thickness of about 0.4 mm. Then, the exposed surface of the osmotic layer is coated with a semipermeable wall. The wall-forming semipermeable composition comprises 92% cellulose acetate having an acetyl content of 36% and 8% polyethylene glycol 4,000 wt/wt. The cellulose acetate is prepared by blending cellulose acetate having an acetyl content of 39.8% with cellulose acetate having an acetyl content of 32% in the ratio of 51.3% to 48.7%, wt/wt.

The semipermeable wall is applied in a air suspension machine. The coating composition comprises 3% polymer solution in methylene chloride-methanol, in the ratio of 80% to 20%, wt/wt. The semipermeable wall around the osmotic layer in initial contacting relation therewith weighed about 21 mg and has a thickness of about 0.05 mm. The osmotic systems, after removal from the air suspension coater is dried in a forced air oven at 40° C. for 48 hours. Then, an orifice having a diameter of 0.92 mm is laser drilled through the respective walls for delivering the vitamin from the osmotic system over a prolonged period of 24 hours.

EXAMPLE 2

The procedure of Example 1 is followed in this example, with the osmotic system as previously described, except that in this manufacture the osmotic system comprises (a) acetaminophen in vegetable oil, (b) ascorbic acid in polysorbate, (c) ephedrine sulfate in vegetable oil, (d) glyceryl guaicolate in peanut oil, (e) mephenesin in polyethylene glycol 400, (f) meprobamate in polyethylene glycol 400, (g) procaine penicillin G in vegetable oil, (h) tetracycline amphoteric in vegetable oil, (i) a composition comprising vitamin A and vitamin D in fish oil, (j) vitamin E in rapeseed oil, (k) theophylline in polyethylene glycol, and (e) estrogen in an emulsified carrier comprising corn oil, sorbitan trioleate, polysorbate and benzyl benzoate.

EXAMPLE 3

An osmotic system for the delivery of the therapeutic vitamin E is prepared as follows: first, a pharmaceutically acceptable soft capsule comprising vitamin E is overcoated on its exterior surface with a composition comprising hydroxypropylmethylcellulose having a 88,000 molecular weight. The overcoat is formed by mixing the hydroxypropylmethylcellulose in water and it is applied to the exterior surface of the capsule in an Aeromatic ® Hi-Coater. The coated dosage form is dried in an oven. Next, the overcoat-capsule assembly is surrounded with a semipermeable wall. The wall is formed from a composition comprising 75 wt % cellulose acetate having an acetyl content of 43.25%, and 25 wt % hydroxypropylcellulose in a cosolvent comprising 80% methylene chloride and 20% methanol to yield a wall forming composition comprising 3% solids. The wall forming composition is prepared by mixing the two solvents and slowly adding the cellulose acetate and the hydroxypropylcellulose until all the solids dissolve in the cosolvent. The composition is added to an Aeromatic ® coater and coated around the overcoat at 40° C. until it is surrounded with a semipermeable wall about 3.4 mil (0.08 mm) thick. The wall weighs about 7.4 mg. The osmotic system is dried in a forced air oven at 50° C. with 50% relative humidity for 2 days and then transferred to a 50° C. forced air oven for 5 days. The dry osmotic system is drilled with a 10 mil (0.256 mm) dispensing passageway to yield the operative osmotic system.

EXAMPLE 4

The procedure of Example 3 is followed in this example with the manufacturing steps as previously described, except that in this example, the overcoat in direct contact with the exterior surface of the soft capsule comprises (1) a composition comprising 80% hydroxypropylmethylcellulose possessing a 27,800 molecular weight, 16% polyvinylpyrrolidone having a 360,000 molecular weight and 4% polyvinylpyrrolidone having a 560,000 molecular weight; (2) a composition comprising 100% hydroxypropylmethylcellulose having a 27,800 molecular weight; and (3) a composition comprising 80% hydroxypropylmethylcellulose having a 27,800 molecular weight and 20% polyvinylpyrrolidone having a 560,000 molecular weight.

EXAMPLE 5

An osmotic system is prepared as follows: a hard, two component capsule comprising a wall comprising gelatin, iron oxide and titanium dioxide, that surrounds and defines an internal lumen containing a drug formulation comprising 100 mg of captopril, water, mint oil and polyethylene glycol is coated on its exterior surface with an osmotic push composition comprising sodium carboxymethylcellulose and water. The sodium carboxymethylcellulose had a 90,000 molecular weight and the dried composition is about 2 mm thick. Next, the middle push layer is surrounded with a semipermeable wall comprising cellulose acetate having an acetyl content of 32% using an air suspension coater. A 5% polymer solution in acetone-water, 90:10 wt/wt, is used for forming a wall 0.075 mm thick. A passageway having a diameter of 0.25 mm is laser drilled through the outside wall and middle layer, with a passageway forming in the inner wall during operation of the osmotic system for delivering the drug in a therapeutically effective amount over time.

EXAMPLE 6

The procedure of Example 5 is followed to provide osmotic systems comprising a soft one piece capsule and a two piece capsule, wherein the internal lumen in each capsule comprises 87 wt % vitamin E oil and 13 wt % of a composition comprising an antioxidant mixture of butylated hydroxytoluene and butylated hydroxyanisole dissolved in benzyl alcohol, the emulsifier polyoxyethylene sorbitan monooleate, and the glyceride glyceryl triester of caproic acid, and wherein the osmotic push layer comprises 100 wt % hydroxypropylmethylcellulose having an 88,400 molecular weight, and a semipermeable wall comprising 60 wt % cellulose acetate having a 39.8% acetyl content, 15 wt % hydroxypropylcellulose and 15 wt % polyethylene glycol.

EXAMPLE 7

The procedure of Example 6 is followed to yield a manufacture wherein the interior lumen comprises 100 wt % vitamin E oil, the capsule wall is 100 wt % gelatin, the osmotic push layer comprises 9 wt % sodium carboxymethylcellulose having a 90,000 molecular weight and 91 wt % sodium carboxymethylcellulose having a 120,000 molecular weight; and the semipermeable wall comprises 60 wt % cellulose acetate having a 39.8% acetyl content, 20 wt % polyethylene glycol, and 20 wt % hydroxypropylcellulose. The osmotic systems comprise one passageway having a 40 mil diameter. The vitamin E drug dose in the osmotic system is equal to 430 mg, and delivers the drug over a prolonged period of 18.5 hours, with a mean release rate of 21.6 mg/hr.

EXAMPLE 8

The procedure of Example 7 is followed in this example to provide an osmotic system wherein the internal lumen comprises 100 wt % vitamin E oil, the push layer comprises 78.88 wt % sodium carboxymethylcellulose comprising a 90,000 molecular weight and 21.12 wt % sodium carboxymethylcellulose comprising a 250,000 molecular weight, and a semipermeable wall comprising 60 wt % cellulose acetate having 39.8% acetyl content, 20 wt % polyethylene glycol and 20 wt % hydroxypropylcellulose, a 40 mil passageway, a release rate of 59.3 mg/hr over 12 hours, and a vitamin drug dose of 760 mg.

EXAMPLE 9

An osmotic system is prepared according to the procedure of Example 1. The capsule wall consists essentially of gelatin, glycerin, sorbitol and water. The capsule contains 50,000 I.U. of vitamin A in olive oil. The osmotic push layer comprises 50 wt % sodium carboxymethyl cellulose having a 90,000 molecular weight and 50 wt % sodium carboxymethylcellulose having a 120,000 molecular weight, and the semipermeable wall encapsulating the osmotic layer consists essentially of 88 wt % cellulose acetate having an acetyl content of 32% and 12% sorbitol. The diameter of the osmotic passageway is about 0.2 mm.

EXAMPLE 10

An osmotic system for the controlled and continuous deliver of the beneficial drug carbocreme chlorhydrate is prepared as follows: a soft capsule or a hard capsule comprising a 0.5 wall that surrounds and forms a closed, hollow inner space is filled with 150 mg of carbocreme chlorhydrate, peanut oil, soy oil and vegetable oil. The capsule is coated with a composition comprising 75 wt % sodium carboxymethylcellulose having 250,000 molecular weight, 5 wt % polyvinylpyrrolidone having a 560,000 molecular weight and 20 wt % hydroxypropylmethylcellulose having a 132,500 molecular weight, and a semipermeable wall formed by blending 170 g of cellulose acetate having an acetyl content of 39.4% in 400 ml of methylene chloride and 400 ml of methanol which is spray coated in an air suspension machine. The coated system is dried for 72 hours at 35° C. and then a 0.9 mm orifice is laser drilled through the semipermeable cellulosic wall and the osmotic layer.

EXAMPLE 11

The procedure of Example 10 is followed with all conditions and procedures as previously indicated except that in this example the drug formulation in the lumen consists essentially of 250 mg of ethosuximide, polyethylene glycol 400, gelatin, glycerine and water.

DISCLOSURE OF METHOD OF USING THE INVENTION

An embodiment of the invention pertains to a method for administering a beneficial drug at a controlled rate to the gastrointestinal tract of a warm-blooded animal, including humans, which method comprises: (A) admitting into the gastrointestinal an osmotic system comprising: (1) a capsule comprising a single body or a capsule comprising a body and a matching cap telescopically joined to define a lumen; (2) a beneficial liquid drug formulation in the lumen comprising a dosage unit amount of drug for performing a therapeutic program; (3) an osmotic layer surrounding the capsule, the osmotic layer comprising a member selected from the group consisting of an osmagent composition and an osmopolymer composition; (4) a wall surrounding the osmotic layer, the wall formed of a semipermeable polymeric composition permeable to the passage of an aqueous and biological fluid and substantially impermeable to the passage of drug formulation; and, (5) an osmotic orifice through the exterior wall, the middle layer and the capsule wall for communicating with the exterior of the osmotic system and the internal lumen; (B) imbibing fluid through the semipermeable wall into the osmotic layer at a rate determined by the permeability of the semipermeable wall and the osmotic pressure gradient across the wall thereby motivating the osmotic layer to absorb fluid, swell and push against the capsule causing the capsule to dynamically pump drug from the lumen; and (C) delivering the beneficial drug formulation in a therapeutically effective amount through the orifice at a controlled rate to the gastrointestinal tract to produce the desired medical effect over a prolonged period of from 15 minutes to 24 hours.

Inasmuch as the foregoing specification comprises preferred embodiments of the invention, it is understood that various variations and modifications can be made herein in accordance with the inventive principles disclosed, without departing from the scope of the invention.

We claim:

1. An osmotic system for delivering a therapeutic drug formulation to an environment of use, wherein the osmotic system comprises:
   (a) a capsule comprising an internal lumen; said capsule formed of gelatin having a viscosity of 15 to 20 millipoises;
   (b) a dosage amount of a therapeutic drug liquid formulation in the capsule lumen;
   (c) a hydroactivated composition on the outside wall of the capsule;
   d) a semipermeable composition surrounding the hydroactivated composition; and,
   e) a passageway that communicates the exterior with the interior of the osmotic system, which passageway is formed by a process selected from the group consisting of drilling, eroding, extracting, dissolving, bursting, and leaching a passageway in the osmotic system.

2. An osmotic system for delivering a therapeutic drug formulation to an environment of use, wherein the osmotic system comprises:
   a) a capsule comprising a gelatin wall having a bloom value of 160 to 250 and an internal lumen;
   b) a dosage amount of a therapeutic drug liquid formulation in the capsule lumen;
   c) a hydroactivated composition on the outside wall of the capsule;
   d) a semipermeable composition surrounding the hydroactivated composition;
   e) a passageway in the osmotic system that connects the exterior with the interior of the osmotic system, and wherein;
   f) the osmotic system is shaped and adapted for admittance into a buccal, implant, anal, cervical, vaginal, subcutaneous, oral and nose environment of use.

* * * * *